(12) United States Patent
Tanimoto et al.

(10) Patent No.: US 6,545,177 B2
(45) Date of Patent: Apr. 8, 2003

(54) COMPLEX OXIDE CATALYST AND PROCESS FOR PREPARATION OF ACRYLIC ACID

(75) Inventors: Michio Tanimoto, Himeji (JP); Daisuke Nakamura, Himeji (JP); Hiromi Yunoki, Himeji (JP)

(73) Assignee: Nippon Shokubai Co. Ltd., Osaka (JP)

( * ) Notice: Subject to any disclaimer, the term of this patent is extended or adjusted under 35 U.S.C. 154(b) by 73 days.

(21) Appl. No.: 09/729,433

(22) Filed: Dec. 5, 2000

(65) Prior Publication Data

US 2001/0003727 A1 Jun. 14, 2001

(30) Foreign Application Priority Data

Dec. 8, 1999 (JP) .......................... 349067/99

(51) Int. Cl.$^7$ .................. C07C 51/235; B01J 23/00
(52) U.S. Cl. .................. 562/535; 562/534; 562/531; 502/306; 502/309; 502/312
(58) Field of Search ................. 562/534, 535, 562/531; 502/306, 309, 312

(56) References Cited

U.S. PATENT DOCUMENTS

| | | | | |
|---|---|---|---|---|
| 3,954,855 A | * | 5/1976 | Wada et al. ............. | 502/178 |
| 4,469,810 A | * | 9/1984 | Kato et al. ............. | 502/209 |
| 5,686,373 A | * | 11/1997 | Tenten et al. ............. | 502/312 |
| 5,739,392 A | * | 4/1998 | Tanimoto et al. ............. | 562/535 |
| 5,981,804 A | * | 11/1999 | Kurimoto et al. ............. | 568/479 |
| 6,069,271 A | * | 5/2000 | Tanimoto et al. ............. | 562/545 |

FOREIGN PATENT DOCUMENTS

| | | |
|---|---|---|
| EP | 0227461 | 7/1987 |
| EP | 0293859 A | 12/1988 |
| EP | 0427508 A | 5/1991 |
| EP | 0756894 A | 2/1997 |
| EP | 0792866 A | 9/1997 |

* cited by examiner

Primary Examiner—Porfirio Nazario-Gonzalez
(74) Attorney, Agent, or Firm—Sherman & Shalloway

(57) ABSTRACT

A catalyst which is a complex oxide catalyst represented by the following general formula (1):

$$Mo_a V_b W_c Cu_d A_e B_f C_g D_h E_i O_x \qquad (1)$$

(in which Mo is molybdenum; V is vanadium, W is tungsten, Cu is copper, A is at least an element selected from antimony, niobium and tin; B is at least an element selected from alkaline earth metals; C is at least an element selected from silicon, aluminum, titanium and zirconium; D is at least an element selected from phosphorus, tellurium, cerium, lead, arsenic and zinc; E is at least an element selected from Group IA and Group IIIb elements of the periodic table, boron, iron, bismuth, cobalt, nickel and manganese; and O is oxygen; a, b, c, d, e, f, g, h, i and x denote the atomic ratios of Mo, V, W, Cu, A, B, C, D, E and O, respectively; and where $a=12$, $2 \leq b \leq 15$, $0 \leq c \leq 10$, $0 < d \leq 6$, $0 \leq e \leq 6$, $0 < f \leq 10$, $0 < g \leq 10$, $0 \leq h \leq 5$, $0 \leq i \leq 5$, and x is a numerical value determined by the extents of oxidation of the other elements) which is characterized by being formed of a complex oxide which is prepared by using, as at least a part of the supply sources of components B and C, a compound containing both of the components B and C is provided. The catalyst is useful for vapor phase catalytic oxidation, in particular, is suitable as a catalyst for preparing acrylic acid by vapor phase catalytic oxidation of acrolein.

8 Claims, No Drawings

COMPLEX OXIDE CATALYST AND PROCESS FOR PREPARATION OF ACRYLIC ACID

FIELD OF INDUSTRIAL UTILIZATION

This invention relates to complex oxide catalysts and production process of acrylic acid. More particularly, the invention relates to complex oxide catalysts suitable for use in producing acrylic acid from acrolein by vapor-phase catalytic oxidation reaction, and to a producing process of acrylic acid from acrolein using said catalysts.

PRIOR ART

A large number of improved catalysts for preparing acrylic acid through vapor phase catalytic oxidation reaction of acrolein have been proposed. For example, Japanese Patent Publication No. 12129/69 described a catalyst formed of molybdenum, vanadium and tungsten; Publication No. 11371/74, that formed of molybdenum, vanadium, copper, tungsten and chromium; Publication No. 25914/75, that formed of molybdenum and vanadium; and Laid-open (Kokai) Patent Application, Kokai No. 85091/77, that formed of molybdenum, vanadium, copper and at least one element of antimony and germanium.

However, these conventional catalysts are not fully satisfactory for industrial working, because of such defects that the yield of the object product, i.e., acrylic acid, is insufficient and deterioration rate in activity is high, leading to short catalyst life. Therefore, development of catalysts which excel in stability and enable acrylic acid production at high yield over prolonged periods has been in demand.

The applicant has disclosed the catalysts containing molybdenum, vanadium and alkaline earth metals in Laid-open (Kokai) Patent Application, Kokai No. 117419/74, which catalysts, however, are still open to improvements in respect of acrylic acid yield and catalyst life.

PROBLEM TO BE SOLVED BY THE INVENTION

Accordingly, one of the objects of the present invention is to provide complex oxide catalysts, in particular, those which are suitable for producing acrylic acid through vapor phase catalytic oxidation of acrolein.

Another object of the present invention is to provide a process for preparing acrylic acid at high yield over prolonged periods, by oxidizing acrolein in the presence of catalyst at vapor phase with molecular oxygen or a molecular oxygen-containing gas.

MEANS TO SOLVE THE PROBLEM

We have discovered that the desired catalysts excelling in activity, selectivity and also catalyst life and which exhibit stable performance over prolonged periods can be obtained in the occasion of preparing a complex oxide catalysts expressed by the following general formula (1):

$$Mo_aV_bW_cCu_dA_eB_fC_gD_hE_iO_x \quad (1)$$

(in which the components and their ratios are as later identified),
when a compound containing both components B and C is used as at least a part of supply sources of components B and C; and that the use of this catalyst enables production of acrylic acid from acrolein at high yield over prolonged periods. Based on these discoveries the present invention is completed.

Namely, the present invention relates to a complex oxide catalyst which is expressed by the following general formula (1):

$$Mo_aV_bW_cCu_dA_eB_fC_gD_hE_iO_x \quad (1)$$

(in which Mo is molybdenum; V is vanadium, W is tungsten, Cu is copper, A is at least an element selected from antimony, niobium and tin; B is at least an element selected from alkaline earth metals; C is at least an element selected from silicon, aluminum, titanium and zirconium; D is at least an element selected from phosphorus, tellurium, cerium, lead, arsenic and zinc; E is at least an element selected from Group IA and Group IIIb elements of the periodic table, boron, iron, bismuth, cobalt, nickel and manganese; and O is oxygen; a, b, c, d, e, f, g, h, i and x denote the atomic ratios of Mo, V, W, Cu, A, B, C, D, E and O, respectively; and where a=12, $2 \leq b \leq 15$, $0 \leq c \leq 10$, $0 < d \leq 6$ (preferably $0.05 \leq d \leq 6$), $0 \leq e \leq 6$, $0 < f \leq 10$ (preferably $0.01 \leq f \leq 10$), $0 < g \leq 10$ (preferably $0.01 \leq g \leq 10$), $0 \leq h \leq 5$, $0 \leq i \leq 5$, and x is a numerical value determined by the extents of oxidation of the other elements)
which is characterized in that a compound containing both of the components B and C is used as at least a part of the supply sources of components B and C at the time of the catalyst preparation.

EMBODIMENTS OF THE INVENTION

Those complex oxide catalysts which are represented by the general formula (1) are per se known as disclosed in said Kokai No. 117,419/74. In the complex oxide catalysts of the invention, preferably antimony and tin are used as the component A; magnesium, calcium, strontium and barium, as the component B; silicon and aluminum, as the component C; phosphorus, tellurium and zinc; as the component D; sodium, potassium, iron, cobalt, nickel and boron, as the component E; respectively.

The characteristic feature of the invention lies in the use of a compound containing both components B and C (which is hereafter referred to as a B/C components-containing compound) as at least a part of supply sources (starting compounds) of components B and C in the occasion of preparing the complex oxide catalysts of the present invention. The reason why the complex oxide catalysts of excellent performance are obtained through such a practice is not yet clear. At the present time we presume that whereby improved stability of the component B contributes to the better performance, while the scope of this invention should never be restricted by this presumption.

The volume ratio of a B/C components-containing compound in the supply sources of components B and C (i.e., total volume of the starting material of component B and that of component C) is 0.5/1 to 1/1, preferably 0.8/1 to 1/1, in terms of the atomic ratio. In particular, it is preferred to supply the total amount of the component B in the catalyst from a B/C components-containing compound.

As the supply sources for Mo, V, W, Cu, components A, D and E; any compounds which contain the named individual elements and which produce the corresponding oxides upon calcination can be used.

As B/C components-containing compounds, any of marketed compounds (preferably oxides) which contain both components B and C can be used as they are. Examples of such marketed oxides include barium aluminate ($2BaO.Al_2O_3.5H_2O$), magnesium silicate ($Mg_2Si_3O_8.5H_2O$), calcium silicate ($CaSiO_3$), barium titanate ($BaTiO_3$), strontium titanate ($SrTiO_3$), calcium titanate (CaTiO₃), calcium zirconate (CaZrO₃) and the like. Other than these commercial products, oxides containing both components B and C can be prepared through, for example, the following procedures: ① dissolve or disperse a component B—containing compound and a component C-containing compound in water, dewater and give such treatments like drying, and thereafter calcine at prescribed temperatures, preferably at 500–2000° C.; ② thoroughly mix a component B—containing oxide with a component C—containing oxide and calcine the mixture at prescribed temperatures, preferably at 500–2000° C.; ③ calcine a B/C components—containing compound at prescribed temperatures, preferably at 500–2000° C.

Said B/C components—containing compounds are preferably used in pulverized state to an average particle diameter of not greater than 200 μm, more advantageously not greater than 100 μm, and most advantageously, not greater than 50 μm.

Where either of the components B and C comprises more than one element, it is sufficient for the B/C components—containing compound to contain at least one of the elements as the component B or C. The B/C components—containing compound may also contain a component other than the components B and C, e.g., component E. Obviously, such a compound is useful also as a supply source of the component E.

The complex oxide catalysts of the invention can be prepared by the methods generally practiced for preparing this kind of complex oxide catalysts, except that a B/C components—containing compound is used as at least a part of the supply sources of the components B and C.

Shape of the complex oxide catalysts of the invention is not critical. They may be molded into any optional forms such as ring, sphere, column, tablet and the like, with an average diameter of 1–15 mm, preferably 3–10 mm. In preparing the catalysts, those well known additives having the effect of improving the strength and attrition resistance of catalysts, such as inorganic fibers, e.g., glass fiber or various whiskers may be added. Also for controlling the catalyst properties with good reproducibility, additives generally known as powder binder such as ammonium nitrate, cellulose, starch, polyvinyl alcohol, stearic acid and the like may be used.

While the complex oxide catalysts of the invention are each useful by itself (as molded catalyst), they are preferably used in the form supported on inert carriers such as alumina, silica-alumina, silicon carbide, silicon nitride, titanium dioxide, aluminium sponge and the like (as supported catalyst). In the latter case, suitable supported ratio (%) of the complex oxide expressed by the general formula (1) ([(weight of the complex oxide)/(weight of the inert carrier+weight of the complex oxide)]×100) is 10–70%, preferably 15–50%.

Production of acrylic acid from acrolein according to the present invention can be performed by any of known methods, except that one of the so far described complex oxide catalysts should be used as the catalyst. The apparatus and operating conditions in carrying out the production are not critical. That is, as the reactor, an ordinary fixed bed reactor, fluidable bed reactor or moving bed reactor can be used, and the reaction can be carried out under the conditions conventionally employed for production of acrylic acid from acrolein through vapor phase catalytic oxidation reaction. For example, a gaseous mixture of 1–15 volume % of acrolein, 0.5–25 volume % of oxygen, 1–30 volume % of steam and 20–80 volume % of an inert gas like nitrogen, is contacted with a complex oxide catalyst of the invention at temperatures ranging from 200 to 400° C., under a pressure of 0.1–1 MPa and at a space velocity of 300–5,000 h⁻¹ (STP) to produce acrylic acid.

Besides such gaseous mixtures of acrolein, oxygen and inert gas, acrolein-containing gaseous mixtures which are obtained through direct oxidation of propylene may also be used as the starting gas, if necessary after adding air or oxygen and steam. Presence of such side products as acrylic acid, acetic acid, carbon oxide and propane or unreacted propylene in the acrolein-containing gaseous mixtures obtained upon direct oxidation of propylene is in no way detrimental to the catalysts used in the process of the invention.

EFFECTS OF THE INVENTION

According to the invention, high-activity and high-performance catalysts are obtainable with good reproducibility. Moreover, because the complex oxide catalysts of the invention maintain the high activity levels over prolonged periods, acrylic acid can be stably produced at high yields over prolonged periods according to the process of the invention.

EXAMPLES

Hereinafter the invention is explained more specifically referring to working Examples, it being understood that the Examples incur no restricting effect on the invention.

In the Examples, the acrolein conversion, acrylic acid selectivity and acrylic acid yield were calculated according to the following formulae:

acrolein conversion (%)=[(mol number of reacted acrolein)/(mol number of fed acrolein)]×100 acrylic acid selectivity (%)=[(mol number of formed acrylic acid)/(mol number of reacted acrolein)]×100 acrylic acid yield (%)=[(mol number of formed acrylic acid)/(mol number of fed acrolein)]×100

Example 1

Preparation of Mg/Si—Al-Containing Compound

Into 200 ml of pure water, 53 g of magnesium nitrate and 7.8 g of aluminium nitrate were dissolved under heating and stirring. To the solution 93 g of 20% by weight silica sol was added, mixed and evaporated to dryness under heating to provide a solid matter. The solid was heat-treated at temperatures elevated stagewisely, followed by 3 hours' calcination at 1,400° C. The product was pulverized to a powder (1) having an average particle diameter of 30 μm.

Preparation of Catalyst

Into 2,000 ml of pure water, 350 g of ammonium paramolybdate, 106 g of ammonium metavanadate and 44.6 g of ammonium paratungstate were dissolved under heating and stirring. Separately, 87.8 g of cupric nitrate and 12 g of antimony trioxide were added to 200 g of pure water under heat and stirring. Thus obtained two liquids were mixed, 11.2 g of the powder (1) was added to the liquid mixture and together poured into a porcelain evaporator on hot water bath. Then, 1,200 ml of a silica-alumina spherical carrier having an average particle diameter of 5 mm was added, followed by evaporation to dryness under stirring to have the catalyst deposited on the carrier. The carrier-supported catalyst was calcined at 400° C. for 6 hours to provide Catalyst (1). The composition of metallic elements (excepting oxygen, as in all of hereafter indicated compositions) of this Catalyst (1) was as follows:

$$Mo_{12}V_{5.5}W_1Cu_{2.2}Sb_{0.5}Mg_{0.5}Si_{0.75}Al_{0.05}.$$

The supported ratio was 23.4%.

Oxidation Reaction

A stainless steel reaction tube of 25 mm in diameter was charged with 1,000 ml of thus obtained Catalyst (1), and into which a gaseous mixture of 5 volume % of acrolein, 5.5 volume % of oxygen, 25 volume % of steam and 64.5 volume % of inert gas comprising nitrogen and the like was introduced. The reaction was carried out at 260° C. and at a space velocity (SV) of 1,500 h$^{-1}$ (STP). The catalyst performance at the initial period and after 8,000 hours' reaction was as shown in Table 1.

Comparative Example 1

Catalyst (2) of the same composition to that of Catalyst (1) was prepared in the identical manner in Example 1, except that "Mg/Si—Al-containing compound" was not prepared but each the same amount to that used in Example 1 of magnesium nitrate, silica sol and aluminum nitrate were used as they ware. Using this Catalyst (2), the oxidation reaction was run under identical conditions with those of Example 1. The result was as shown in Table 1.

Example 2

Preparation of Sr/Si—Al-Containing Compound

To 74.4 g of 20 weight % silica sol, 10.7 g of strontium oxide, 0.6 g of cobalt nitrate and 10.5 g of aluminum oxide were added, mixed and evaporated to dryness under heating to form a solid matter. The solid was heat-treated at temperatures elevated stagewisely, followed by 3 hours' calcination at 1,500° C. Pulverizing the product, a powder (2) having an average particle diameter of 30 μm was obtained.

Preparation of Catalyst

Into 2,000 ml of pure water, 350 g of ammonium paramolybdate, 116 g of ammonium metavanadate and 53.5 g of ammonium paratungstate were dissolved under heating and stirring. Separately, into 200 g of pure water, 99.8 g of cupric nitrate and 12 g of antimony trioxide were added under heating and stirring. The so formed two liquids were mixed, 28.9 g of the powder (2) was added, and together poured into a porcelain evaporator on hot water bath. Then 1,200 ml of a silica-alumina spherical carrier having an average particle diameter of 5 mm was added, followed by evaporation to dryness under stirring to have the catalyst deposited on the carrier. The carrier-supported catalyst was calcined at 400° C. for 6 hours to provide Catalyst (3). The composition of the metallic elements in this Catalyst (3) was as follows:

$$Mo_{12}V_6W_{1.2}Cu_{2.5}Sb_{0.5}Sr_{0.5}Si_{1.2}Al_1Co_{0.01}.$$

The supported ratio was 24.8%.

Oxidation Reaction

The reaction was carried out under identical conditions with those in Example 1, except that Catalyst (1) was replaced with Catalyst (3). The result was as shown in Table 1.

Example 3

Preparation of Ca—Ba/Si—Al-Containing Compound

Into 200 ml of pure water, 48.8 g of calcium nitrate, 54 g of barium nitrate and 0.9 g of sodium nitrate were dissolved under heating and stirring. To this solution 335 g of 20 weight % silica sol and 33.7 g of aluminum oxide were added, mixed and evaporated to dryness under heating to provide a solid matter. Thus obtained solid was heat-treated at temperatures elevated stagewisely, followed by 3 hours' calcination at 1,400° C. Pulverizing the product, a powder (3) having an average particle diameter of 30 μm was obtained.

Preparation of Catalyst

Into 2,000 ml of pure water, 350 g of ammonium paramolybdate, 96.6 g of ammonium metavanadate and 44.6 g of ammonium paratungstate were dissolved under heating and stirring. Separately, 99.8 g of cupric nitrate was dissolved in 200 g of pure water under heating and stirring. Thus formed two solutions were mixed, to which 115.5 g of the powder (3) was added and together poured into a porcelain evaporator on hot water bath. Then 1,200 ml of a silica-alumina spherical carrier having an average particle diameter of 5 mm was added and evaporated to dryness to have the catalyst deposited on the carrier, followed by 6 hours' calcination at 400° C. to provide Catalyst (4). The composition of the metallic elements of this Catalyst (4) was as follows:

$$Mo_{12}V_5W_1Cu_{2.5}Ca_1Ba_1Si_{5.4}Al_{3.2}Na_{0.05}.$$

The supported ratio was 26.7%.

Oxidation Reaction

The reaction was carried out under identical conditions with those in Example 1, except that Catalyst (1) was replaced with Catalyst (4). The result was as shown in Table 1.

Example 4

Preparation of Mg/Si—Al-Containing Compound

Into 400 ml of pure water, 12.7 g of magnesium nitrate, 0.2 g of potassium nitrate and 1.0 g of iron nitrate were dissolved under heating and stirring. Into this solution 220 g of 20 wt % silica sol and 1.8 g of aluminum oxide were added, mixed and evaporated to dryness under heating to provide a solid matter. The solid was heat-treated under temperatures raised stagewisely, followed by 3 hours' calcination at 1,200° C. The product was pulverized to provide a powder (4) having an average particle diameter of 30 μm.

Preparation of Catalyst

Into 2,000 ml of pure water, 350 g of ammonium paramolybdate, 116 g of ammonium metavanadate and 67 g of ammonium paratungstate were dissolved under heating and stirring. Separately, 99.8 g of cupric nitrate was dissolved in 200 g of pure water under heating and stirring. Thus formed two solutions were mixed, and to which 186 g of the powder (4) was added and together put into a porcelain evaporator on hot water bath. Then 1,200 ml of a silica-alumina spherical carrier having an average diameter of 5 mm was added, followed by evaporation to dryness under stirring to have the catalyst deposited on the carrier. The supported catalyst was calcined at 400° C. for 6 hours to provide Catalyst (5). The composition of the metallic elements in this Catalyst (5) was as follows:

$$Mo_{12}V_6W_{1.5}Cu_{2.5}Mg_{0.2}Si_{0.3}Al_{0.02}K_{0.01}Fe_{0.01}.$$

The supported ratio was 23.8%.

Oxidation Reaction

The reaction was carried out under identical conditions with those in Example 1, except that Catalyst (1) was replaced with Catalyst (5). The result was as shown in Table 1.

Example 5

Preparation of Mg/Si-Containing Compound

One-hundred (100) g of magnesium silicate manufactured by Nakarai Tesqu Co. was calcined at 1,500° C. for 3 hours to obtain a powder (5).

Preparation of Catalyst

Into 2,000 ml of pure water, 350 g of ammonium paramolybdate, 96.6 g of ammonium metavanadate and 53.5 of ammonium paratungstate were dissolved under heating and stirring. Separately, 87.8 g of cupric nitrate, 13.0 of titanium dioxide and 4.8 g of antimony trioxide were added to 200 g of pure water under heating and stirring. Thus obtained two liquids were mixed, 51.7 g of the powder (5) was added to the liquid mixture and together put into a porcelain evaporator on hot water bath. Then 1,200 ml of a silica-alumina spherical carrier having an average particle diameter of 5 mm was added and evaporated to dryness under stirring to have the catalyst deposited on the carrier. The supported catalyst was then calcined at 400° C. for 6 hours to provide Catalyst (6). The composition of the metallic elements of this Catalyst (6) was as follows:

$$Mo_{12}V_5W_{1.2}Cu_{2.2}Sb_{0.2}Mg_{2.4}Si_{3.6}Ti_1.$$

The supported ratio was 25.0%.

Oxidation Reaction

The reaction was carried out under identical conditions with those in Example 1, except that Catalyst (1) was replaced with Catalyst (6). The result was as shown in Table 1.

TABLE 1

|  | Catalyst No. |  | Reaction Temp. (° C.) | Acrolein conversion (%) | Acrylic Acid Selectivity (%) | Acrylic Acid Yield (%) |
|---|---|---|---|---|---|---|
| Example 1 | (1) | Initial stage of reaction | 260 | 99.1 | 96.0 | 95.1 |
|  |  | After 8,000 hrs. | 268 | 99.2 | 95.8 | 95.0 |
| Comparative Example 1 | (2) | Initial stage of reaction | 260 | 97.0 | 93.8 | 91.0 |
|  |  | After 8,000 hrs. | 291 | 97.8 | 93.1 | 91.1 |
| Example 2 | (3) | Initial stage of reaction | 260 | 99.6 | 95.6 | 94.4 |
|  |  | After 8,000 hrs. | 267 | 99.4 | 95.4 | 94.8 |
| Example 3 | (4) | Initial stage of reaction | 260 | 99.0 | 95.4 | 94.4 |
|  |  | After 8,000 hrs. | 272 | 99.0 | 95.3 | 94.3 |
| Example 4 | (5) | Initial stage of reaction | 260 | 99.0 | 95.8 | 94.8 |
|  |  | After 8,000 hrs. | 271 | 99.2 | 95.7 | 94.9 |
| Example 5 | (6) | Initial stage of reaction | 260 | 99.1 | 95.2 | 94.3 |
|  |  | After 8,000 hrs. | 274 | 99.0 | 94.9 | 94.0 |

What is claimed is:

1. A process for preparing acrylic acid through oxidation of acrolein at vapor phase with molecular oxygen or a molecule oxygen-containing gas in the presence of a catalyst, using a complex oxide catalyst having the general formula (1)

$$Mo_aV_bW_cCu_dA_eB_fC_gD_hE_iO_x \quad (1)$$

wherein
Mo is molybdenum;
V is vanadium;
W is tungsten;
Cu is copper;
A is at least an element selected from antimony, niobium and tin;
B is at least an element selected from alkaline earth metals;
C is at least an element selected from silicon, aluminum, titanium and zirconium;
D is at least an element selected from phosphorus, tellurium, cerium, lead, arsenic and zinc;
E is at least an element selected from Group IA and Group IIIb elements of the periodic table, boron, iron, bismuth, cobalt, nickel and manganese;
O is oxygen;
a, b, c, d, e, f, g, h, i and x denote the atomic ratios of Mo, V, W, Cu, A, B, C, D, E and O, respectively where a–12, $2 \leq b \leq 15$, $0 \leq c \leq 10$, $0 \leq d \leq 6$, $0 \leq e \leq 6$, $0 < f \leq 10$, $0 < g \leq 10$, $0 \leq h \leq 5$, $0 \leq I \leq 5$, and x is a numerical value determined by the extent of oxidation of the other elements; and wherein said complex oxide is prepared by using, as at least a part of the supply sources of components B and C, a B/C compound containing both of the components B and C.

2. The process of claim 1, wherein the component B is selected from the group consisting of magnesium, calcium, strontium, and barium.

3. The process of claim 1, wherein the component C is selected from the group consisting of silicon and aluminum.

4. The process of claim 1, wherein the B/C compound is heat treated at 500–2000° C.

5. The process of claim 1, wherein the B/C compound is in a pulverized state and has an average particle diameter of not greater than 200 μm.

6. The process of claim 5, wherein the B/C compound is in a pulverized state and has an average particle diameter of not greater than 100 μm.

7. The process of claim 6, wherein the B/C compound is in a pulverized state and has an average particle diameter of not greater than 50 μm.

8. The process of claim 1, wherein the ratio of the B/C compound to either component B or C is in a range from about 0.5/1 to 1/1, in terms of the atomic ratio.

* * * * *